(12) United States Patent
Cadwalader et al.

(10) Patent No.: US 7,667,214 B2
(45) Date of Patent: Feb. 23, 2010

(54) RADIATION ATTENUATION SYSTEM

(75) Inventors: John A. Cadwalader, Overland Park, KS (US); G. David Dixon, Leawood, KS (US)

(73) Assignee: Worldwide Innovations & Technologies, Inc., Overland Park, KS (US)

( * ) Notice: Subject to any disclaimer, the term of this patent is extended or adjusted under 35 U.S.C. 154(b) by 202 days.

(21) Appl. No.: 11/122,327

(22) Filed: May 4, 2005

(65) Prior Publication Data

US 2006/0251219 A1    Nov. 9, 2006

(51) Int. Cl.
*G21F 3/00*   (2006.01)

(52) U.S. Cl. ............... 250/515.1; 250/517.1; 250/519.1

(58) Field of Classification Search ............... 250/515.1
See application file for complete search history.

(56) References Cited

U.S. PATENT DOCUMENTS

| | | | |
|---|---|---|---|
| 2,794,128 A * | 5/1957 | Shasky | 250/519.1 |
| 2,942,115 A * | 6/1960 | O'Connell | 250/517.1 |
| 4,286,170 A | 8/1981 | Moti | |
| 4,386,277 A | 5/1983 | Forshee | |
| 4,638,166 A * | 1/1987 | Baudro | 250/515.1 |
| 4,859,184 A * | 8/1989 | Hazard | 433/136 |
| 5,022,099 A | 6/1991 | Walton | |
| 5,220,175 A * | 6/1993 | Cole | 250/515.1 |
| 5,550,383 A | 8/1996 | Haskell | |
| 6,035,450 A | 3/2000 | Monsen, III et al. | |
| 6,325,538 B1 * | 12/2001 | Heesch | 378/203 |

* cited by examiner

*Primary Examiner*—David A. Vanore
*Assistant Examiner*—Phillip A. Johnston
(74) *Attorney, Agent, or Firm*—Foley & Lardner LLP

(57) ABSTRACT

A radiation attenuation system for shielding from scatter radiation one or more portions of a patient that are not of primary interest to a particular radiological procedure (i.e., non-target areas, etc.). The radiation attenuation system may be configured to shield the head of a patient (such as the head of a pediatric patient), and/or any other portion of the patient that may benefit from being shielded from scatter radiation. The radiation attenuation system is preferably configured to conform to the contours of the patient. The radiation attenuation system may be a flexible member that can be reconfigured to accommodate patients of varying size.

17 Claims, 9 Drawing Sheets and
RADIATION ATTENUATION SYSTEM

FIELD

The present invention relates generally to systems for and methods of attenuating radiation. More particularly, the present invention relates to systems for and methods of shielding a patient from secondary or scatter radiation during a radiological procedure (e.g., fluoroscopy, radiographic procedures, etc.). One embodiment of the present invention further relates to systems for and methods of shielding the head of an infant, toddler, child, and/or adolescent (i.e., pediatric patients) from secondary or scatter radiation.

BACKGROUND

Radiation is used in a variety of medical procedures (generally referred to herein as "radiological procedures"). For example, radiation is used in diagnostic procedures (i.e., procedures allowing non-invasive investigation of a patient), therapeutic procedures (i.e., procedures wherein discrete anatomical regions of a patient are irradiated as a treatment), and various invasive procedures such as fluoroscopic guidance and/or manipulation of instruments during surgical procedures.

Radiation is a valuable tool, but one which may require certain safeguards. Living tissue is susceptible to damage through high intensity, prolonged, and/or repeated exposure to radiation. Scatter radiation is a secondary radiation generated when the primary radiation interacts with the object being impinged. Scatter radiation has a frequency range lower than the primary radiation beam and generally moves in a variety of uncontrollable directions. Scatter radiation, like primary radiation, can cause damage to living tissue.

It is well documented that radiation exposure is cumulative. Although the amount of scatter radiation exposure that a patient receives during a single radiological procedure may not be harmful, a patient who undergoes a great number of such procedures may suffer damage due to the cumulative effect of scatter radiation. Studies demonstrate that the cumulative effect of scatter radiation may cause greater damage to an infant, toddler, child, and/or adolescent (i.e., pediatric patients) than to an adult patient. Such studies suggest that repeated exposure of scatter radiation to the head of a pediatrics patient may affect their cognitive ability as they develop.

Thus, there is a need for a radiation attenuation system for and method of shielding one or more non-target areas of a patient from scatter radiation. There is also a need for a radiation attenuation system that is configured to shield the head of patient from scatter radiation. There is further a need for a radiation attenuation system that is configured to shield the head of a pediatric patient. Yet further, there is a need for a radiation attenuation system that is configured to shield the head of a infant. There is further a need for a radiation attenuation system having a configuration that may reduce the tension or stress experienced by a patient during a radiological procedure. There is also a need for a radiation attenuation system that can be easily shipped and/or stored. There is further a need for radiation attenuation system addressing these, and/or any other need.

SUMMARY

One embodiment of the present invention relates to a radiation attenuation system for shielding the head of a pediatric patient from scatter radiation during radiological procedure. The system includes a radiation attenuating barrier having a first region and an opposite second region. The second region is configured to conform to the neck of the pediatric patient. The system further includes a support member coupled to the radiation attenuating barrier for supporting the radiation barrier in a generally upright in-use position. The radiation attenuating barrier is configured to be positioned perpendicular to a longitudinal axis of the pediatric patient.

Another embodiment of the present invention relates to a radiation attenuation system for shielding a patient from scatter radiation during a radiological procedure. The system includes a radiation barrier having a lower region defining an aperture for conforming to a portion of the patient, means for supporting the radiation barrier in a generally upright position, and means for selectively reconfiguring the position of the lower region to minimize gaps between the patient and the radiation barrier.

A further embodiment of the present invention relates to a method of attenuating scatter radiation during a radiological procedure. The method comprises the steps of placing a radiation attenuation system between a target area on a patient and non-target area on the patient, manipulating the radiation attenuation system so that a portion of the radiation attenuation system at least partially conforms to the patient, positioning the radiation attenuation system in a generally upright position, and exposing the target area on the patient to a primary radiation beam.

BRIEF DESCRIPTION OF THE DRAWINGS

Exemplary embodiments of the present invention will hereafter be described with reference to the accompanying drawings, wherein like numerals denote like elements, and.

DETAILED DESCRIPTION

Referring to FIGS. 1 through 9, a radiation attenuation system 20 and components thereof are shown according to exemplary embodiments. Generally, radiation attenuation system 20 includes one or more radiation shields or barriers supported in a manner and at a position that may be useful in attenuating (e.g., blocking, reflecting, absorbing, etc.) secondary or scatter radiation generated during a radiological procedure (i.e., any medical procedure wherein radiation is applied to a patient). Radiation attenuation system 20 is configured to shield one or more portions of the patient that are not of primary interest to the particular radiological procedure (i.e., non-target areas, etc.). According to a preferred embodiment, radiation attenuation system 20 is configured to shield the head of the patient from scatter radiation during a radiological procedure being performed on a lower portion of the patient.

It should be noted that while the exemplary embodiments are described and illustrated herein as a radiation attenuation system for shielding the head of a patient, and more particularly, as a radiation attenuation system for shielding the head of a patient who is an infant, toddler, child, and/or adolescent (collectively referred to herein as a "pediatric patient"), the radiation attenuation system may be configured to shield other non-target areas of the patient. For example, radiation attenuation system 20 may be configured to shield the gonadal, abdominal, torso, and/or extremity regions of a patient, and/or any other area of the patient that may benefit from being shielded from scatter radiation. Further, radiation attenuation system 20 may be sized and configured to be used with non-pediatric patients (e.g., adult patients, etc.).

Further still, radiation attenuation, system 20 may be used in a variety of radiological procedures including, but not limited to, diagnostic procedures (i.e., procedures allowing non-invasive examination or investigation of a patient such as x-ray examinations, CT scanning procedures, or the like), therapeutic procedures (i.e., procedures wherein anatomical regions of a patient are irradiated as a treatment), and/or various invasive procedures (e.g., procedures wherein a patient is irradiated for guiding the manipulation of instruments, etc.). Also, radiation attenuation system 20 may be used regardless of the position of the patient. For example, the patient may be provided in a supine position wherein the patient is positioned on his or her back with the legs of the patient being straight or bent, a prone position wherein the patient is positioned face down, and/or a lateral position wherein the patient is positioned on one side.

Figure 1:
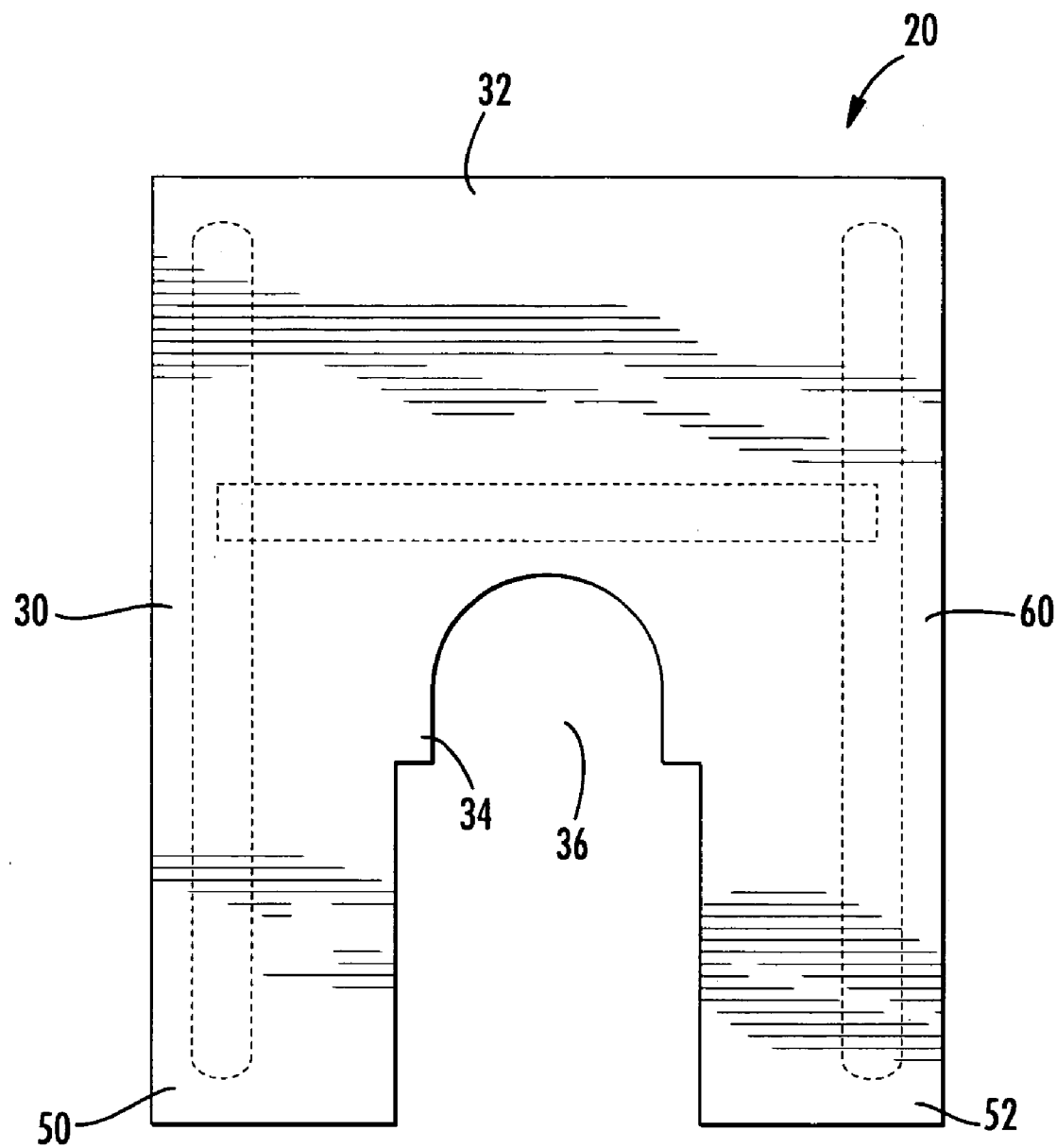
FIG. 1 is a front planar view of a radiation attenuation system according to an exemplary embodiment.

FIG. 1 is a front view showing radiation attenuation system 20 according to an exemplary embodiment. Radiation attenuation system 20 is shown in a relatively flattened or extended position (i.e., a non-in-use position or storage position). Radiation attenuation system 20 generally comprises one or more radiation shields or barriers 30 for attenuating scatter radiation and protecting a portion of a patient. Barrier 30 is shown as a substantially rectangular member having a first or upper region (e.g., edge, periphery, portion, etc.), shown as a first margin 32, and a second or lower region, shown as a second margin 34.

Second margin 34 is intended to be positioned adjacent to (e.g., proximate, near, at, etc.) a patient and/or a patient support structure (e.g., medical table, diagnostic surface, examination table, patient stretcher, etc.) and includes a configuration suitable for allowing barrier 30 to substantially conform to the contours of the patient. According to an exemplary embodiment, second margin 34 is shown as having a cutout or missing portion, shown as an aperture 36, that is shaped and dimensioned to substantially conform to the contours of the neck of a typical pediatric patient. Aperture 36 is defined by an edge 38 of second margin 34 having a curvilinear shape (e.g., arcuate, semi-circular, etc.). According to various alternative embodiments, aperture 36 may have any of a variety of shapes, including shapes having linear portions, non-linear portions, or combinations thereof.

Figure 3:
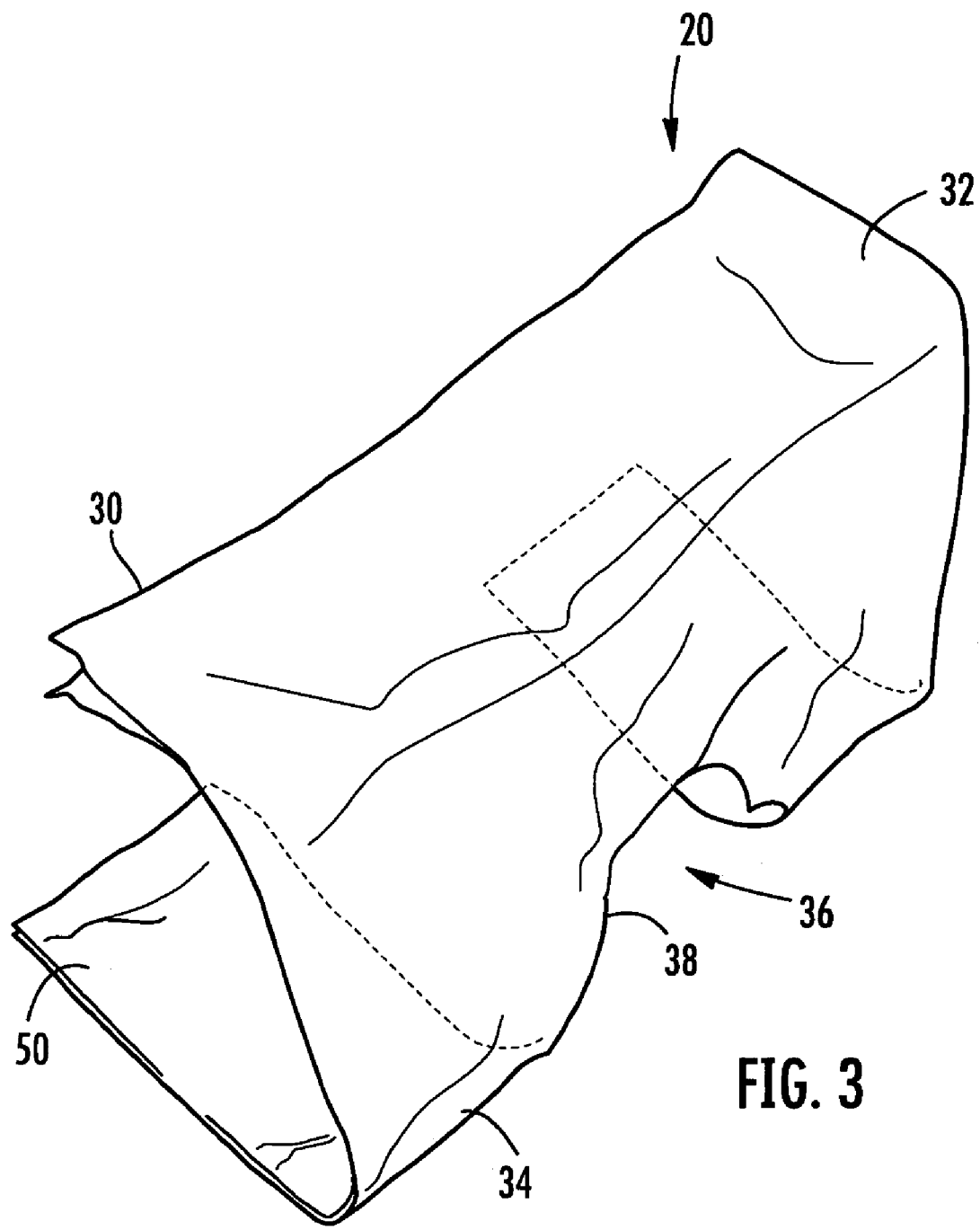
FIG. 3 is a perspective view of the radiation attenuation system illustrated in FIG. 1 shown in an in-use position.

Referring further to FIG. 1, radiation attenuation system 20 is also shown as comprising first and second legs 50, 52 which are used to support radiation attenuation system 20 in an in-use position (shown in FIG. 3). First and second legs 50, 52 are positioned adjacent to second margin 34 of barrier 30, and are shown in a first or storage position in which first and second legs 50, 52 are substantially disposed within the same plane as barrier 30. First and second legs 50, 52 are configured to move between the first position (shown in FIG. 1) and a second or in-use position (shown in FIG. 3). Configuring radiation attenuation system 20 as a member that can be substantially flattened may facilitate in the shipping and/or storing of radiation attenuation system 20. According to an alternative embodiment, first and second legs 50, 52 may be fixed in an in-use position. Preferably, first and second legs 50, 52 are integrally formed with barrier 30, but alternatively may be provided as separate components.

Figure 2:
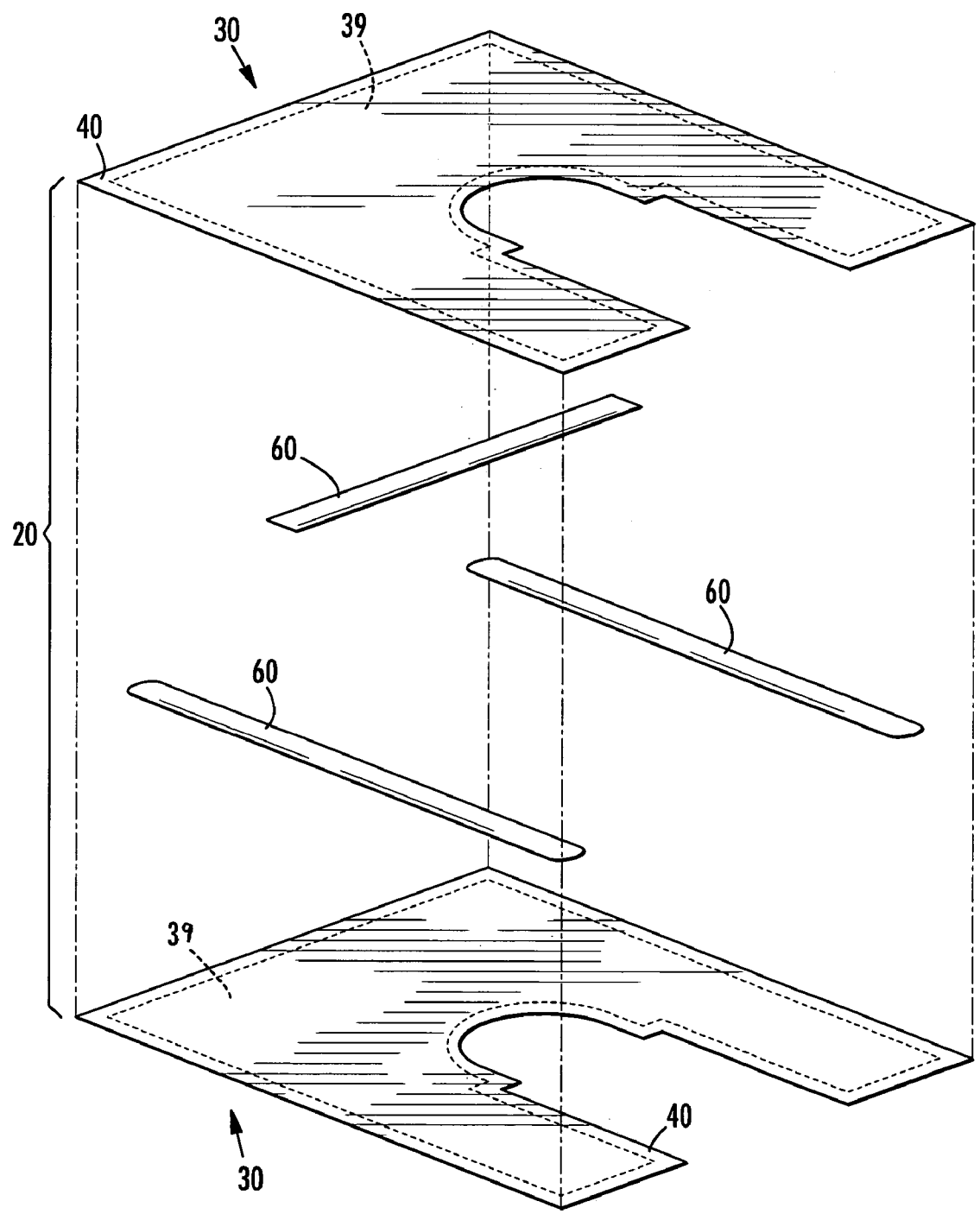
FIG. 2 is an exploded view of the radiation attenuation system illustrated in FIG. 1.

FIG. 2 shows an exploded view of radiation attenuation system 20. For the illustrated embodiment, radiation attenuation system 20 is shown as utilizing more than one barrier 30 (e.g., a front barrier and a back barrier, etc.). Each barrier 30 includes a radiation attenuating member or pad 39 (shown in dashed lines) made of a radiation attenuating material. Preferably, the radiation attenuating material is generally light and flexible to maximize workability for bending, folding, reconfiguring, etc., or otherwise manipulating barrier 30. The material may be formable (e.g. deformable) or compliant, and/or relatively "stretchable" (e.g. elastic). According to alternative embodiments, the material used may be generally rigid and inflexible (as in the exemplary embodiment shown in FIG. 9), and/or substantially weighted.

Radiation attenuating pad 39 may be fabricated of any radiation attenuation material including, but not limited to, bismuth, barium, lead, tungsten, antimony, copper tin, aluminum, iron, iodine, cadmium, mercury, silver, nickel, zinc, thallium, tantalum, tellurium, and uranium. Anyone of the aforementioned radiation attenuation materials alone or in a combination of two or more of the radiation attenuation materials may provide the desired level of radiation attenuation. Preferably, the radiation attenuating material is comprised of a polymeric matrix charged with an attenuating filler. Examples of suitable radiation attenuation materials for radiation attenuating pad 39 are disclosed in U.S. Pat. No. 4,938,233, entitled "Radiation Shield," and U.S. Pat. No. 6,674,087, entitled "Radiation Attenuation System," both of which are hereby incorporated by reference in their entirety. It should be noted that radiation attenuating pad 39 is not limited to such radiation attenuating materials, and according to various alternative embodiments may be formed of any suitable radiation attenuating material including more conventional attenuating materials.

The radiation transmission attenuation factor of radiation attenuating pad 39 may vary depending upon the intended application of radiation attenuation system 20 and/or the number of barriers 30 provided. According to one exemplary embodiment, radiation attenuating pad 39 has a radiation transmission attenuation factor of a percent (%) greater than about 50%, suitably greater than about 90%, suitably greater than about 95% (with reference to a 100 kVp x-ray beam). According to various alternative embodiments; radiation attenuating pad 39 may have a radiation transmission attenuation factor of a percent less that 50% such as 10-50% or 10-20%. Radiation attenuating pad 39 may also at least partially attenuate gamma rays, and may have a gamma ray attenuation factor of at least 10% of a 140 keV gamma radiation source.

Referring further to FIG. 2, each barrier 30 is shown having a covering 40 disposed about or containing radiation attenuating pad 39. Covering 40 may enhance processability, provide softness or comfort to a patient, and/or may allow radiation attenuation system 20 to be more easily cleaned and/or sanitized. Covering 40 is preferably made of a fabric material such as that of a surgical drape, but can also be made of a non-fabric material such as a plastic sheet, non-woven paper material, or any other material suitable for covering radiation attenuating pad 39. According to an exemplary embodiment, covering 40 is constructed from a front sheet and a back sheet which are coupled together at the periphery to enclose radiation attenuating pad 39.

For purposes of this disclosure, the term "coupled" means the joining or combining to two or more members (e.g., portions, layers, materials, components, etc.) directly or indirectly to one another. Such joining or combining may be relatively stationary (e.g., fixed, etc.) in nature or movable (e.g., adjustable, etc.) in nature. Such joining or combining may be achieved with the two members or the two members and any additional intermediate members being integrally formed as a single unitary body with one another (e.g., one-piece, etc.) or with the two members or the two members and any additional intermediate member being attached to one another. Such joining or combining may be intended to be relatively permanent in nature or alternatively may be intended to be relatively detachable or removable in nature.

Covering 40 may be configured so that it permanently encloses radiation attenuating pad 39, or alternatively may be configured so that radiation attenuating pad 39 may be selectively removed. According to an alternative embodiment, barrier 30 may include a radiation attenuating pad 39 that is not enclosed by a covering 40. According to another alternative embodiment, barrier 30 may include a covering 40 that is integrally formed with a radiation attenuating pad 39.

Radiation attenuation system 20 further comprises one or more support members 60 for supporting radiation attenuation system 20 in an in-use position (shown in FIG. 3). Preferably, support members 60 are malleable (e.g., flexible, impressible, pliable, etc.) members that can be configured and reconfigured with minimal effort by a physician and/or medical assistant so that radiation attenuation system 20 can accommodate patients of varying size and/or to allow radiation attenuation system 20 to be selectively moved to a position that does not substantially interfere with the particular radiological procedure. According to an exemplary embodiment, support members 60 are strips or bands that can be folded or bent into any of a number of positions and can then be returned to a substantially flattened positioned for storage and/or disposal of radiation attenuation system 20. The strips or bands may be formed of metal, plastic, or any other suitable material.

According to various alternative embodiments, support members 60 may be provided by a variety of know or otherwise suitable components that can support radiation attenuation system 20 in the in-use position. For example, support members 60 may be generally rigid and inflexible members which have been set in an in-use position. According to a further alternative embodiment, support members may be unnecessary if barrier 30 is formed of a material that can sufficiently support radiation attenuation system 20 in the in-use position without the need of additional support (as in the exemplary embodiment shown in FIG. 9).

Referring further still to FIG. 2, radiation attenuation system 20 is shown as having a pair of support members 60 extending in a substantially vertical direction relative to barrier 30 and a third support member 60 extending in a substantially horizontal direction. The vertical support members 60 are shown extending between barrier 30 and first and second legs 50, 52. According to an alternative embodiment, separate support members 60 may be provided for barrier 30 and first and second legs 50, 52. The horizontal support member 60 may extend from one vertical support member 60 to the other vertical support member (as shown) or alternatively may extend only partially therebetween. Support members 60 are shown as being sandwiched between barriers 30. Preferably, support members 60 are coupled to one or more of barriers 30 and/or first and second legs 50, 52. Support members 60 may be coupled to barrier 30 and/or first and second legs 50, 52 using any of a variety of known or otherwise suitable techniques including, but not limited to, mechanical fasteners (e.g., hook and loop, clips, snaps, etc.), adhesives, welding, bonding, fusing, stitching, etc. According to an alternative embodiment, support members may be supported at a desired position as a result of being sandwiched between two or more barriers 30.

If more than one barrier 30 is utilized (as shown in FIG. 2), the plurality of barriers 30 may be coupled to each other using any known or otherwise suitable technique. For example, barriers 30 may be coupled using mechanical fasteners, adhesives, welding, bonding, fusing, stitching, etc. Barriers 30 may be intended to be permanently coupled to each other, or alternatively may be intended to be detachably coupled to each other. According to an alternative embodiment, radiation attenuation system 20 may include a single barrier 30. Such a barrier 30 may comprise one or more layers of a radiation attenuation material. If a single barrier 30 is provided, support members 60 may be disposed at a front and/or back side of barrier 30, or alternatively may be integrally formed with barrier 30.

According to a preferred embodiment, one or more of the components of radiation attenuation system 20 (e.g., barrier 30, including covering 40 and/or radiation attenuating pad 39, support members 60, an additional covering, etc.) may be generally disposable in whole or in part, thereby minimizing ancillary sources of contamination that may arise from multiple uses. According to another suitable embodiment, one or more of the components of radiation attenuation system 20 are generally non-toxic, recyclable, and/or biodegradable. According to an alternative embodiment, one or more of the components of radiation attenuation system 20 may be reusable. According to a preferred embodiment, one or more of the components of radiation attenuation system 20 may be sterilized between uses to minimize the likelihood of bacteriological or virus contamination. Sterilization may be performed in any convenient manner, including gas sterilization and irradiation sterilization.

FIG. 3 is a front perspective view showing radiation attenuation system 20 in an in-use position. In the in-use position, first and second legs 50, 52 have been selectively reconfigured so that they are substantially perpendicular to at least a portion of barrier 30. The in-use position is obtained by manipulating (e.g., bending, shaping, etc.) support members 60 until the desired position is achieved. In the in-use position, first and second legs 50, 52 can be placed upon a surface (e.g., a patient support structure, etc.) and they will support barrier 30 in a generally upright position.

For purposes of this disclosure, the phrase "generally upright" is used broadly to define to any position in which barrier 30 may be moved to that is suitable for shielding the head of a patient. Design criteria and application parameters may affect the definition of "generally upright." For example, "generally upright" may describe barriers that have a linear and/or a non-linear trajectories, that extend upward in a substantially vertical direction, and/or that extend upward at any angle ranging from approximately 0 degrees to approximately 90 degrees. Accordingly, all such definitions of "generally upright" are included in the scope of the appended claims.

In FIG. 3 first margin 32 is shown as being folded or bent backwards relative to the remaining portions of barrier 30. Such positioning, as detailed below, may enhance the effectiveness in shielding the head of a patient from scatter radiation. According to various alternative embodiments, first margin 32 and/or other portions of barrier 30 may be selectively moved to a variety of positions. For example, first margin 32 may be substantially aligned with second margin 34 so that barrier 30 is vertically orientated relative to first and second legs 50, 52, and/or may be folded or bent in a forward direction.

Figure 4:
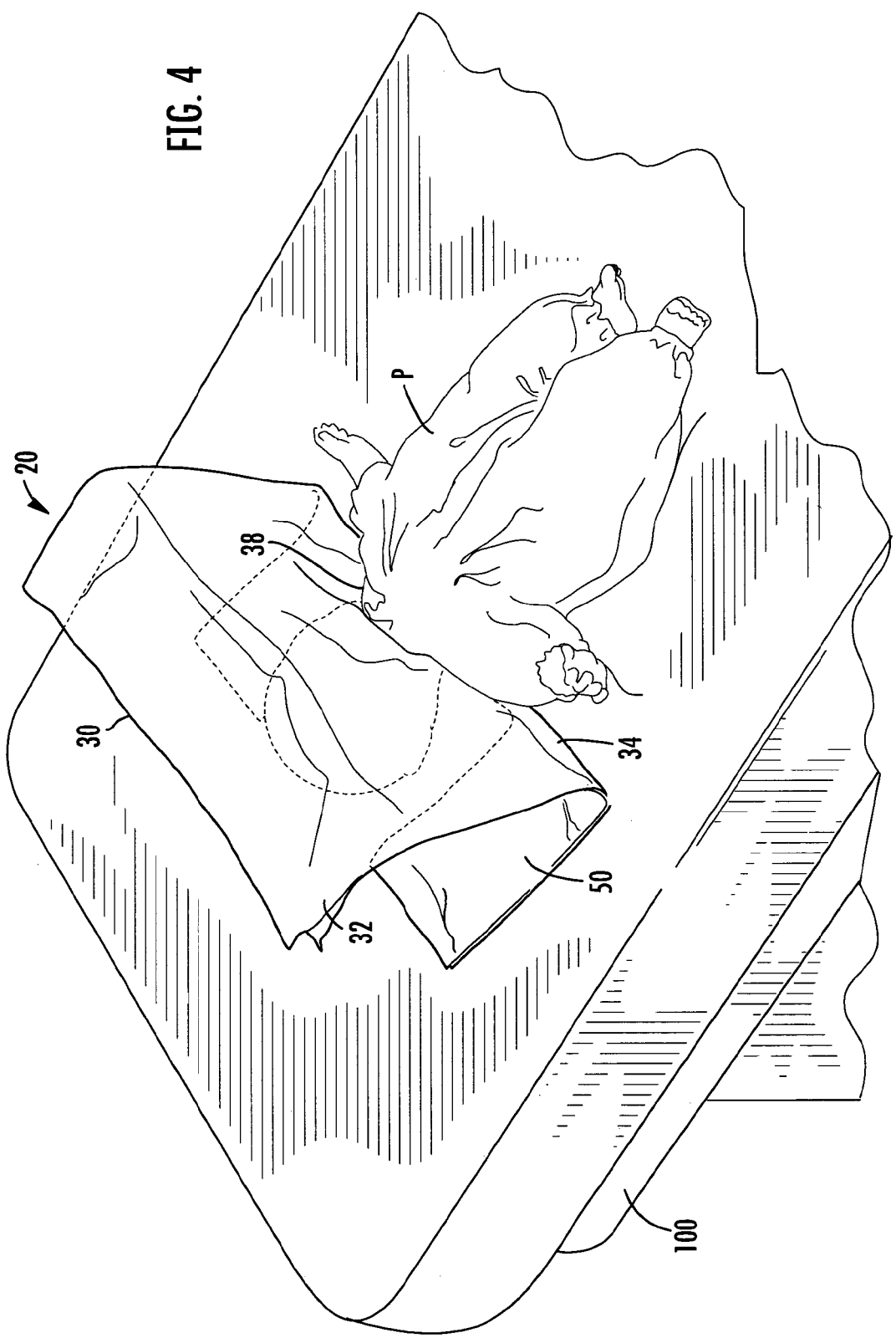
FIG. 4 is a front perspective view of a radiation attenuation system illustrated in FIG. 1 shown shielding the head of a pediatric patient.

FIG. 4 is a front perspective view showing radiation attenuation system 20 being used with a patient P who is positioned on a patient support structure, shown as a patient table 100. Radiation attenuation system 20 is disposed about patient P in manner and at a position intended to reduce the amount of scatter radiation received by the head of patient P during a radiological procedure wherein the target area is a lower portion of patient P. Particularly, aperture 36 is shown as receiving the neck of patient P. Preferably, support members 60 which dictate the positioning of first and second legs 50, 52 and/or second margin 34 can be manipulated so that edge 38 substantially conforms to the contours of the neck patient P without providing significant discomfort to patient P and/or without leaving a significant space or gap between the neck of patient P and edge 38.

Depending on the neck size of patient P, the point at which first and second legs 50, 52 are bent backwards relative to second margin 34 may vary. For example, if patient P has a relatively small structure, it may be beneficial to bend first and second legs 50, 52 closer to second margin 34 than if patient P has a relatively large structure.

Preferably, radiation attenuation system 20 is configured so that the weight of radiation attenuation system 20, or a substantial portion thereof, is not carried by patient P, but is instead carried by another structure such as patient table 100. Such a configuration may be particularly advantageous when radiation attenuation system 20 is used with pediatric patients who may not have the strength to carry the weight of radiation attenuation system 20 even though radiation attenuation system 20 is preferably light in weight. While patient P is not required to carry a substantial portion of the weight of radiation attenuation system 20, it may still be desirable to allow a portion of barrier 30 (e.g., second margin 34, edge 38, and/or an additional drape, etc.) to drape across or otherwise come in contact with patient P in an attempt to limit the number of gaps between patient P and radiation attenuation system 20.

Figure 5:
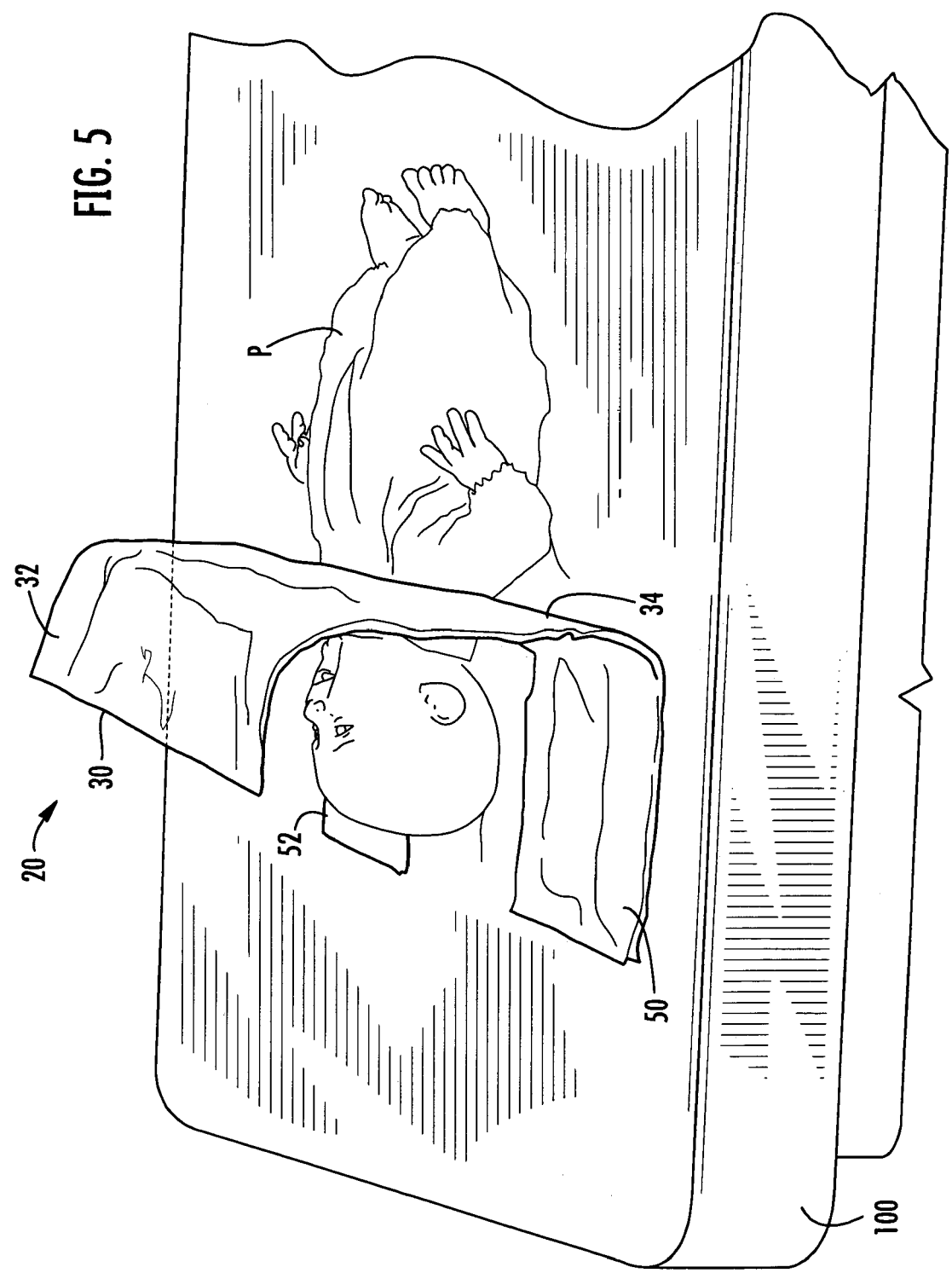
FIG. 5 is a side perspective view of the radiation attenuation system illustrated in FIG. 1 shown shielding the head of a pediatric patient.

FIG. 5 is a side perspective view of radiation attenuation system 20 being used on pediatric patient P. According to an exemplary embodiment, radiation attenuation system 20 is configured to both shield the head of patient P and reduce the amount distress or trauma that will be experienced by patient P during the radiological procedure. Radiation attenuation system 20 may reduce trauma to patient P by having a generally open (e.g., non-enclosing, etc.) disposition when disposed about the neck of patient P. As shown in FIG. 5, radiation attenuation system 20 is generally open to the surrounding environment on the sides, back, and partially on the top. Such openness may allow personnel (e.g., physicians, medical assistants, parents, etc.) to comfort (e.g., distract, entertain, support, etc.) patient P during the radiological procedure by gaining access to patient P and/or by allowing patient P to see and/or hear personnel attempting to comfort patient P.

The method of using radiation attenuation system 20 is described herein with reference to FIGS. 4 and 5. Prior to a radiological procedure in which the primary area of interest (i.e., the target area) of the radiological procedure is at a lower portion of patient P, a physician, medical assistant, and/or any other personnel obtains radiation attenuation system 20. When first obtained, radiation attenuation system 20 may be in a relatively flattened or extended position. The physician (or other personnel) then moves first and second legs 50, 52 backwards by manipulating support members 60 and places radiation attenuation system 20 over patient P so that aperture 36 receives the neck of the patient. The positioning of first and second legs 50, 52 may be further adjusted to obtain the desired fit around the neck of patient P.

During the radiological procedure, a primary radiation beam is applied to a lower portion of patient P. As the primary radiation beam is applied to patient P, scatter radiation is generated due to the interaction of the primary beam with patient P, patient table 100, and/or any other object in the path of the primary radiation beam. The scatter radiation tends to be directed in all directions. Barrier 30 shields the head of patient P from this scatter radiation. First margin 32 of barrier 30 may be bent backwards in an attempt to further shield the head of patient P from scatter radiation that may come over the top of radiation attenuation system 20.

Figure 6:
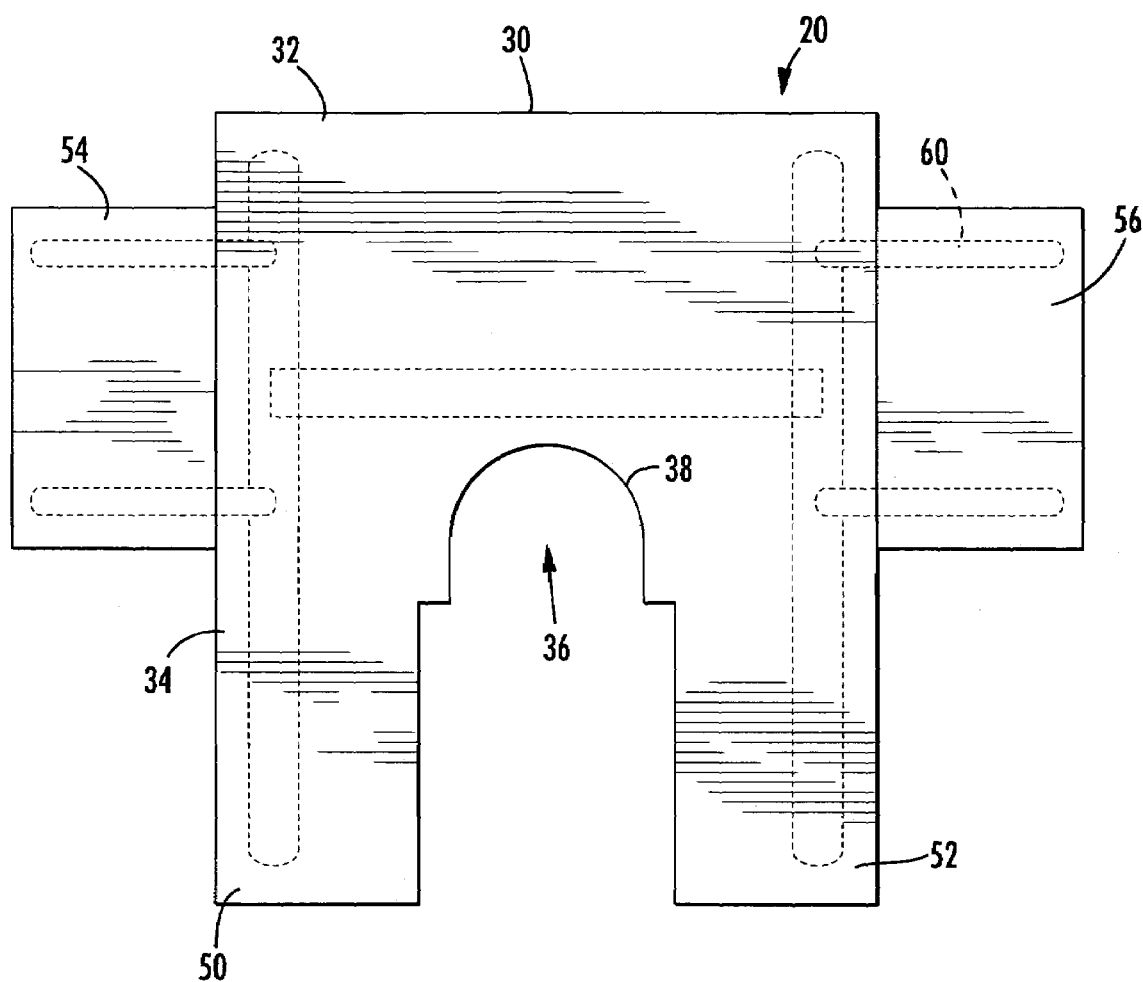
FIG. 6 is a front view of a radiation attenuation system according to another exemplary embodiment.

Referring next to FIG. 6, radiation attenuation system 20 is shown according to another exemplary embodiment. Radiation attenuation system 20 of FIG. 6 is similar to radiation attenuation system 20 of FIG. 1, but is further shown as including one or more supplemental (e.g., auxiliary, add-on, etc.) members, shown as a pair of side flaps 54, 56. Side flaps 54, 56 are provided to further shield a patient from scatter radiation. Similar to first and second legs 50, 52, side flaps 54, 56 are intended to be manipulated, and are configured to move between a first or storage position (shown in FIG. 6) and a second or in-use position (shown in FIG. 7).

Preferably, side flaps 54, 56 have the same construction as barrier 30. According to one exemplary embodiment, side flaps 54, 56 are integrally formed with barrier 30 and extend outwardly therefrom. Alternatively, side flaps 54, 56 may be provided as separate components that are coupled to barrier 30 and/or first and second legs 50, 52. Side flaps 54, 56 are further shown as including one or more support members 60 for allowing side flaps 54, 56 to be selectively moved to a variety of positions. The additional support members 60 are shown extending substantially perpendicular to the vertical support members 60, but alternatively may be provided in some other position.

Figure 7:
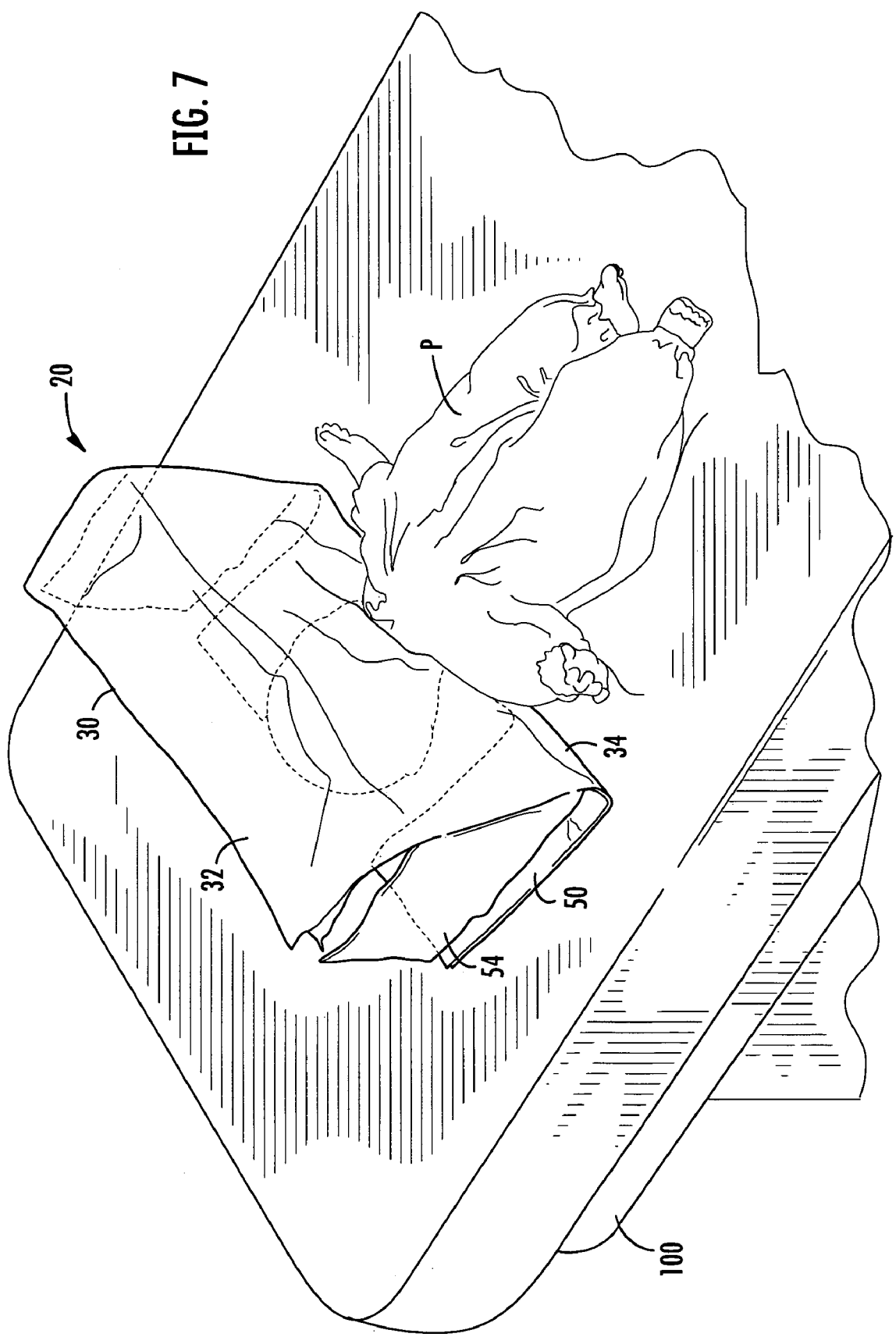
FIG. 7 a front perspective view of a radiation attenuation system illustrated in FIG. 6 shown shielding the head of a pediatric patient.

FIG. 7 is a front perspective view showing radiation attenuation system 20 of FIG. 6 being used with patient P. Side flaps 54, 56 are shown as having been selectively manipulated so that side flaps 54, 56 extend backwards from barrier 30 to further enclose and shield the head of patient P from scatter radiation. In such a position, side flaps 54, 56 are disposed in substantially parallel planes that are substantially perpendicular to a plane in which a portion of barrier 30 is disposed within. In this in-use position, side flaps 54, 56 may further shield the head of patient P by attenuating scatter radiation that may come around the side of radiation attenuation system 20. According to an alternative embodiment (not shown), side flaps 54, 56 may extend to patient table 100 and may be configured to at least partially support radiation attenuation system 20 in the in-use position. In such an embodiment, first and second legs 52, 54 may be eliminated if side flaps 54, 56 can support barrier 30 in a generally upright position.

Figure 8:
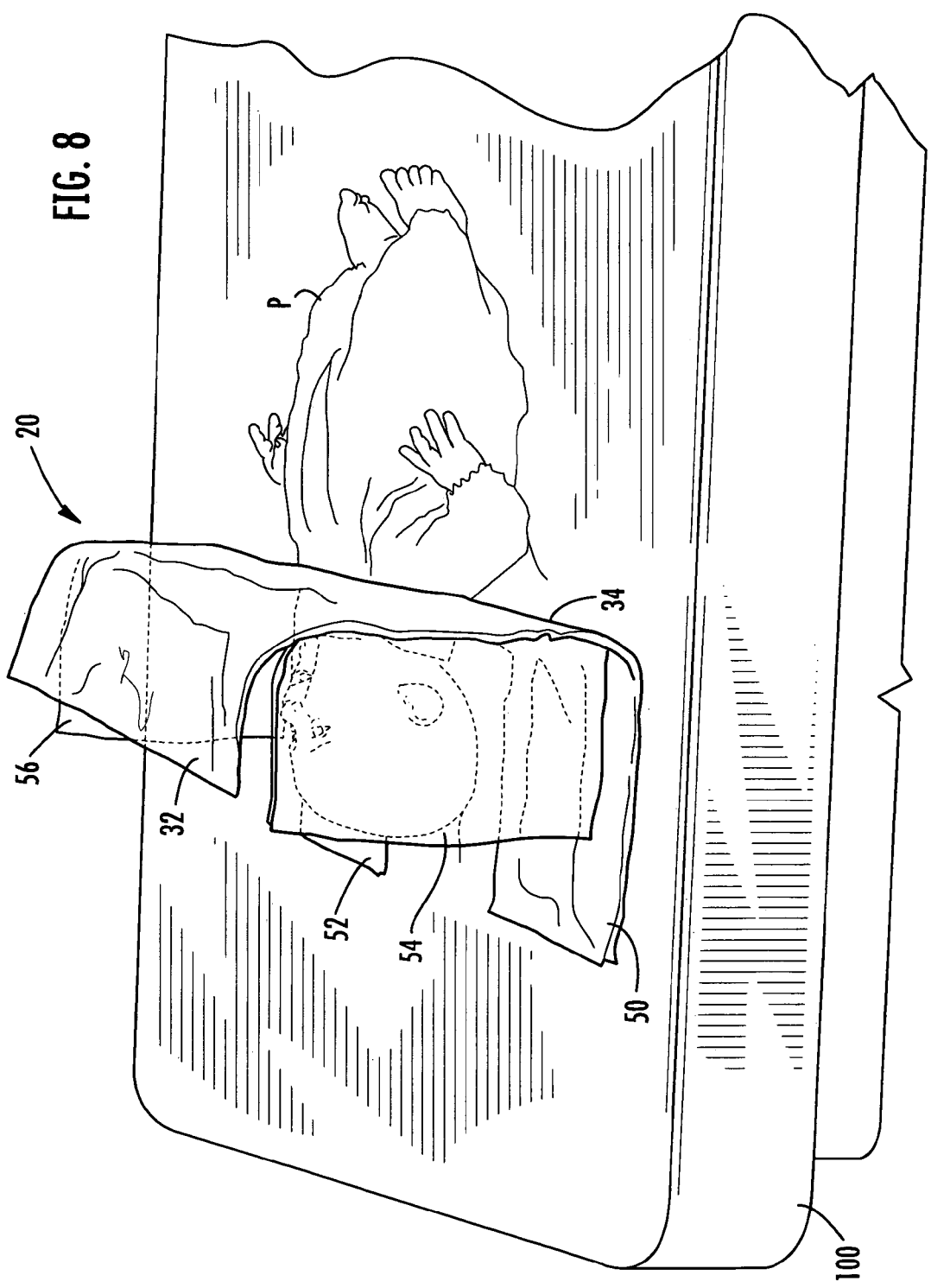
FIG. 8 is a side perspective view of the radiation attenuation system illustrated in FIG. 6 shown shielding the head of a pediatric patient.

FIG. 8 is a side perspective view of radiation attenuation system 20 of FIG. 6. As shown in FIG. 5, radiation attenuation system 20 remains generally open to the surrounding environment at the back and partially at the top, while is partially enclosed along the sides. While gaps are shown between side flap 54 and first margin 32 and patient table 100, according to various alternative embodiments, side flap 54 may be configured so that one or more of such gaps is eliminated.

Figure 9:
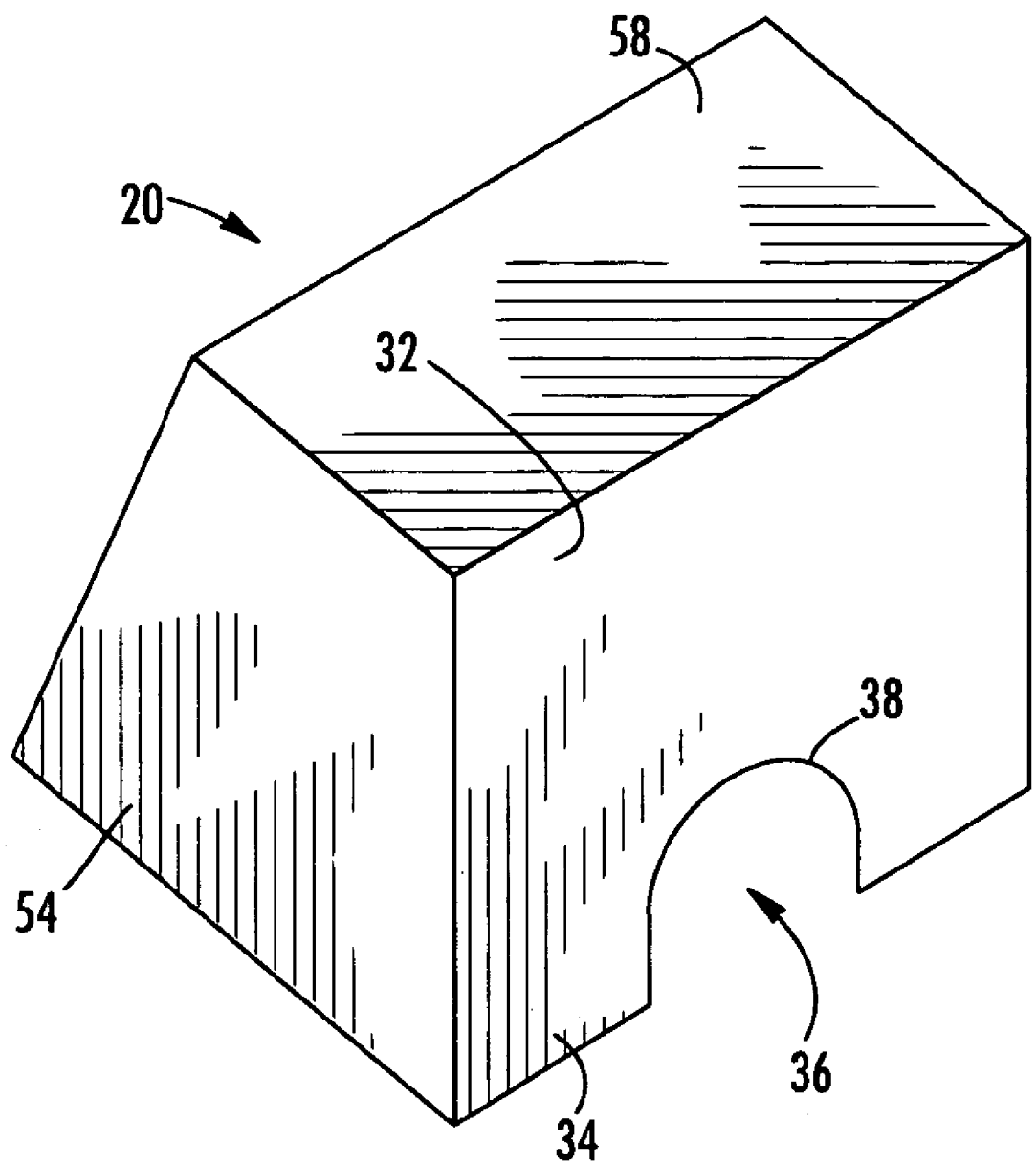
FIG. 9 is a front perspective view of a radiation attenuation system according to still another exemplary embodiment.

FIG. 9 shows radiation attenuation system 20 according to another exemplary embodiment. Radiation attenuation system 20 of FIG. 9 is shown as box-like structure wherein barrier 30 provides a front wall, side flaps 54, 56 provide a pair of side walls, and a top wall is provided by a member 58. In such an embodiment, barrier 30 and side flaps 54, 56 are formed of a substantially rigid material so that the need for support members 60 is eliminated. Similar to the above described embodiments, second margin 34 of barrier 30 defines aperture 36 which is configured to receive the neck of a patient.

It is important to note that the construction and arrangement of the elements of the radiation attenuation system as shown in the illustrated embodiments is illustrative only. Although only a few embodiments of the present inventions have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements shown as multiple parts may be integrally formed, the operation of the interfaces may be reversed or otherwise varied, or the length or width of the structures and/or members or connectors or other elements of the system may be varied. It should be noted that the elements and/or assemblies of the system may be constructed from any of a wide variety of materials that provide sufficient strength or durability, in any of a wide variety of colors, textures and combinations. For example, the radiation attenuation material may be a relatively flexible material, or alternatively, may be a relatively rigid material. Further, barrier 30 may not include an aperture 36, but instead may be configured to conform to the contours of a patient by being formed of a material that can be draped across the patient without applying a significant amount of weight to the patient. Accordingly, all such modifications are intended to be included within the scope of the present inventions. Other substitutions, modifications, changes and omissions may be made in the design, operating conditions and arrangement of the preferred and other exemplary embodiments without departing from the spirit of the present inventions.

The order or sequence of any process or method steps may be varied or re-sequenced according to alternative embodiments. In the claims, any means-plus-function clause is intended to cover the structures described herein as performing the recited function and not only structural equivalents but also equivalent structures. Other substitutions, modifications, changes and omissions may be made in the design, operating configuration and arrangement of the preferred and other exemplary embodiments without departing from the spirit of the inventions as expressed in the appended claims.

What is claimed is:

1. A method of attenuating scatter radiation during a radiological procedure in which a patient is supported on a patient table, the method comprising:
    reconfiguring a self-supporting radiation attenuation system between a substantially flat storage position and a generally upright position;
    placing a radiation attenuation system between a target area on the patient and a non-target area on the patient so that the radiation attenuation system shields the non-target area on the patient without enclosing the target area on the patient;
    manipulating a first portion of the radiation attenuation system to be orientated in a substantially upright position with a lower region that at least partially conforms to the patient;
    manipulating a second portion of the radiation attenuation system to engage the patient table for supporting the entire weight of the radiation attenuation system and for stabilizing the first portion in the substantially upright position; and
    exposing the target area on the patient to a primary radiation beam.

2. The method of claim 1 further comprising placing the radiation attenuation system around the neck of the patient for shielding the head of the patient from scatter radiation.

3. The method of claim 2 further comprising the step of manipulating a third portion of the radiation attenuation system to at least partially enclose the non-target area on the patient.

4. The method of claim 3 wherein the step of manipulating the third portion of the radiation attenuation system to at least partially enclose the non-target area on the patient comprises bending a top portion of the radiation barrier backwards towards the head of the patient to further shield the head of the patient.

5. A self-supporting radiation attenuation system for shielding the head of a patient supported on a patient table during a radiological procedure being conducted on a target area of the patient, the system comprising:
    a barrier formed of a radiation attenuating material and having a lower region with an area configured to receive the neck of the patient when in a use position, the barrier being configured to extend in a substantially upright orientation and perpendicular to a longitudinal axis of the patient when in the use position; and
    a first and second legs coupled to the lower region of the barrier, the first and second legs support the entire weight of the barrier against the patient table and stabilize the barrier in the substantially upright orientation when the barrier is in the use position, the first leg being provided at a first lateral side of the area configured to receive the neck of the patient, the second leg being provided at a second lateral side of the area configured to receive the neck of the patient; the first and second legs being configured to extend substantially perpendicular to the barrier when in the use position,
    wherein the system is selectively reconfigurable between a substantially flat storage position and the use position, and
    wherein the system shields the head of the patient without enclosing the target area of the patient.

6. The system of claim 5 wherein the area configured to receive the neck of the patient the second region is an aperture configured to conform to the neck of the patient.

7. The system of claim 5 wherein the first and second legs are substantially parallel and coplanar to the barrier when in the storage position.

8. The system of claim 5 further comprising a support system extending between the barrier and the first and second legs which allows the system to remain in a selectively reconfigured position, the support system comprising at least one malleable member.

9. A self-supporting radiation attenuation system for shielding a head of a patient supported on a patient table during a radiological procedure being conducted on a target area of the patient, the system comprising:

a barrier including a first portion and a second portion formed of a radiation attenuating material, the second portion configured to be orientated in a generally upright position during use and having a lower region defining an aperture configured to receive a neck of the patient, the first portion coupled to the second portion and extending from an upper region of second portion at an orientation that allows the first portion to at least partially cover the head of the patient during use; and a first leg and a second leg, the first leg extending from the lower region of the second portion on a first side of the aperture, the second leg extending from the lower region of the second portion on a second side of the aperture, the first side leg and the second side leg support the entire weight of the barrier against the patient table and stabilize the second portion in the generally upright orientation during use, wherein the system shields the head of the patient without enclosing the target area of the patient.

10. The system of claim 9 wherein the second portion is configured to be substantially perpendicular to the first portion during use.

11. The system of claim 9 wherein the orientation of the first portion relative to the second portion is selectively adjustable.

12. The system of claim 9 wherein the first portion and the second portion are selectively adjustable so that the system can be moved to a substantially flat storage position.

13. The system of claim 9 wherein the first portion is integrally formed with the second portion to provide a one-piece shield.

14. The system of claim 9 further comprising a support system extending between the first portion and the second portion, the support system comprising at least one malleable member that can be selectivity manipulated to allow the first portion to be supported at a number of orientations relative to the second portion.

15. The system of claim 9 further comprising a first side flap and a second side flap, the first side flap extending from a first lateral side region of the second portion, the second side flap extending from a second lateral side region of the second portion, the first side flap and the second side flap configured to at least partially enclose the head of the patient during use.

16. The system of claim 15 wherein the first portion, the second portion, the first flap and the second flap are selectively adjustable so that the system can be moved to a substantially flat storage position.

17. The system of claim 9 wherein the first portion, the first leg and the second are configured to extend in the same direction from the second portion during use and be substantially parallel to each other.

\* \* \* \* \*